United States Patent [19]

Upchurch

[11] Patent Number: 5,427,234
[45] Date of Patent: Jun. 27, 1995

[54] DISPOSAL OF USED MEDICAL PRODUCTS

[76] Inventor: Gregory E. Upchurch, 762 Whispering Meadows Dr., Manchester, Mo. 63021

[21] Appl. No.: 590,935
[22] Filed: Oct. 1, 1990
[51] Int. Cl.⁶ ............................................. B65D 81/18
[52] U.S. Cl. .................................. 206/210; 206/365; 604/199
[58] Field of Search ............... 206/365, 366, 210, 205; 215/247; 604/199, 263

[56] References Cited

U.S. PATENT DOCUMENTS

| | | | |
|---|---|---|---|
| 1,694,768 | 12/1928 | Cook | 206/210 |
| 2,264,313 | 12/1941 | Humphrey | 206/366 |
| 2,346,725 | 4/1944 | Butzke | 206/366 |
| 2,400,722 | 5/1946 | Swan | 206/210 |
| 2,958,332 | 11/1960 | Schueler | 206/366 |
| 3,354,881 | 11/1967 | Bloch | 604/199 |
| 4,154,342 | 5/1979 | Wallace | 604/199 |
| 4,301,936 | 11/1981 | Percarpio | 215/247 |
| 4,416,663 | 11/1983 | Hall | 604/163 |
| 4,635,807 | 1/1987 | Knapp | 215/247 |
| 4,848,569 | 7/1989 | Leishman | 206/365 |
| 4,921,491 | 5/1990 | Champ | 604/199 |
| 4,936,449 | 6/1990 | Conard et al. | 206/366 |

FOREIGN PATENT DOCUMENTS 0336069 10/1930 United Kingdom ................ 206/365

*Primary Examiner*—Jimmy G. Foster
*Attorney, Agent, or Firm*—Polster, Lieder Woodruff & Lucchesi

[57] ABSTRACT

A disposal device especially suited for used hypodermic needles and other such sharp contaminated medical devices includes a container having a hollow interior and at least one opening through the walls of the container into the container interior, and a plug filling the opening in the container walls and secured to the container. The plug is composed of a resilient, self-sealing, non-coring, needle-penetrable material, so that the used medical product may be inserted through the plug such that at least the tip thereof is in communication with the hollow interior of the container. An anti-microbic, anti-viral liquid is disposed in the hollow interior of the container so that the tip of the used medical product inserted in the hollow interior is exposed to the anti-microbic, anti-viral liquid. The container/plug combination is sufficiently light that it may be agitated by moving the used medical product without the user having to actually touch the container. When the medical device is a needle/syringe combination, liquid from the container may be repeatedly drawn into the syringe barrel from the container and expelled back into the container to insure thorough deactivation of microbes or viral particles present in the needle and the lower portion of the syringe barrel. After this cleansing action is completed, the medical device is not removed from the container. Rather the used medical device and the container are placed as a unit in a disposal receptacle.

4 Claims, 2 Drawing Sheets

DISPOSAL OF USED MEDICAL PRODUCTS

BACKGROUND OF THE INVENTION

This invention relates to infection control, and more particularly to disposal of sharp, contaminated medical devices such as needles.

It is known that used medical products are a source of infection, from both microbial and viral agents. Hepatitis and AIDS (acquired immune deficiency syndrome) are two examples of viral infections known to be transmitted by contaminated medical products such as syringe needles. As a result, these used medical products are handled very carefully for disposal. Unfortunately, this careful handling is not always sufficient to prevent infection. Needle sticks of medical personnel, for example, is a recognized problem of long standing.

There are devices designed to solve the problem of needle sticks, but they could be improved. For example, there are sheaths which come with the needles which prevent needle sticks before the needles are used. However, these devices are typically long and slender and require the medical professional to hold the sheath in one hand while moving the needle into the sheath with the other hand to "resheath" the needle. Resheathing has become a major source of needle sticks. Furthermore, even if resheathing were desirable, it is not always possible to find the sheath which fits the particular needle which the medical professional wants to resheath at a given time.

Rubber stoppers are also used for resheathing. These devices may be placed on a table, thereby obviating the need to hold them in one hand while moving the needle with the other. However, rubber stoppers do have some disadvantages. Needles can pass through them easily, thereby exposing the medical professional to the renewed risk of a needle stick. Sometimes, needles also slip out of the rubber stoppers completely, again exposing the user to a renewed risk of a needle stick. These devices do nothing to kill or inactivate the infectious agents, so any failure of the devices is critical.

It is also known that dilute solutions of household chlorine bleach are effective in killing or inactivating infectious agents. Therefore, authorities have recommended cleaning used needles in bleach before reusing the needles. This procedure, however, is not suggested for single-use, disposable needles (which make up the bulk of the needles used by healthcare professionals), and it is not practical for use in the hospital or doctor's office because of the necessity of carrying a cleaning kit along with the medical professional on his or her rounds.

SUMMARY OF THE INVENTION

Among the various objects and features of the present invention may be noted the provision of an improved disposal device for sharp contaminated medical products.

Another object is the provision of such a disposal device which is relatively inexpensive in construction.

A third object is the provision of such a disposal device which is relatively small and light, so that a medical professional may easily carry a supply.

A fourth object is the provision of such a disposal device which has the capability of killing or inactivating infectious agents.

A fifth object is the provision of such a disposal device which is easy to use.

A sixth object is the provision of such a disposal device which need not be touched during the disposal procedure.

A seventh object is the provision of an improved method of disposing of sharp, contaminated medical products.

An eighth object is the provision of such a disposal device which may be interchangeably used on a variety of sizes and types of used medical products.

Other objects and features will be in part apparent and in part pointed out hereinafter.

Briefly, the disposal device of the present invention is designed to safely dispose of sharp, contaminated medical products, such as needles. The disposal device includes a container having a hollow interior and at least one opening through the walls of the container into the container interior. A plug fills the opening in the container walls and is secured to the container. The plug is composed of a resilient, self-sealing, non-coring, needle-penetrable material, so that a used medical product such as a needle may be inserted through the plug such that at least the tip thereof is in communication with the hollow interior of the container. An anti-microbic, anti-viral liquid is disposed in the hollow interior of the container so that the tip of the used medical product inserted in the hollow interior is exposed to the anti-microbic, anti-viral liquid.

A disposal product of the present invention includes a used medical device such as a needle, having a tip at the end of a shaft, a hollow container having an opening to the interior thereof, and a plug sealing the opening and secured to the container. The plug is self-sealing, non-coring, and needle penetrable. An anti-microbic, anti-viral liquid is disposed in the interior of the hollow container. The tip of the used medical device is disposed in the interior of the hollow container in communication with the liquid. The shaft of the used medical device is disposed through the self-sealing plug, the shaft being held in place by the plug.

A method of the present invention relates to disposing of sharp contaminated medical products having a sharpened tip, such as needles. The method includes the steps of inserting the sharpened tip of a used medical product such as a needle through a plug into the hollow interior of a container, the hollow interior containing an anti-microbic, anti-viral liquid, agitating the liquid in the container without manually touching the container to cause at least the tip of the used medical product to come into intimate contact with the anti-microbic, anti-viral liquid, and placing the container and the used medical product as a unit in a disposal receptacle, with the tip of the medical product still disposed in the container.

In a second aspect of the method of the present invention, the method includes the steps of inserting the sharpened tip of a used medical product such as a needle through a plug into the hollow interior of a container, the hollow interior containing an anti-microbic, anti-viral liquid, so that at least the tip of the medical product is in contact with the anti-microbic, anti-viral liquid, the plug functioning to hold the used medical product in place, and placing the container and the used medical product, with the container secured to the used medical product by the plug, as a unit in a disposal receptacle.

BRIEF DESCRIPTION OF THE DRAWINGS

Similar reference characters indicate similar parts throughout the several views of the drawings.

DESCRIPTION OF THE PREFERRED EMBODIMENT

Figure 1:
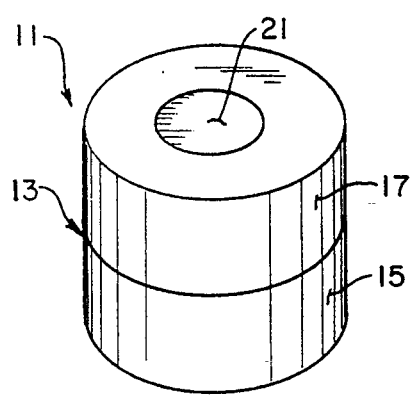
FIG. 1 is a perspective view of a disposal device of the present invention.

A disposal device 11 of the present invention has two parts: a closed, unvented airtight container 13 (shown in FIGS. 1 and 2 as a two-part container consisting of an open-mouthed container 15 forming the bottom and sides of the container and a rubber plug 17 forming the top surface of the container) having a hollow interior, and an anti-microbic, anti-viral material 19 disposed in the hollow interior of the container.

The open-mouthed container 15 is preferably formed of an inexpensive, rigid moldable plastic which is resistant to or relatively inert in the presence of the anti-microbic, anti-viral material 19. The thickness of the walls of the open-mouthed container will vary depending upon the material used, but they should be thick enough to prevent accidental puncture of the walls by a hypodermic needle. Open-mouthed container 15 is preferably made of plastic rather than glass to reduce the overall weight of the disposal device 11. The surface of the container opposite the needle-penetrable surface 17 must especially be relatively needle-impenetrable to prevent the user from pushing a needle or other sharp medical product completely through the disposal device.

Rubber plug 17 can of course be replaced by a layer of a suitable plastic. What is required of the plug material is that it be non-coring, needle-penetrable, and relatively resistant to anti-microbic, anti-viral material 19. It is preferred that the plug material also be resilient and self-sealing. If a plastic material rather than a rubber plug is used to close container 13, it may be attached to the rest of the container in any number of ways. It is required, however, that the container as a whole be water-tight or liquid-tight, so as to not let any of the anti-microbic, anti-viral material escape from container 13 during shipping and handling.

The anti-microbic, anti-viral material 19 may be any of a variety of such materials. Ordinary chlorine bleach (typically having a concentration of active chlorine compounds of approximately 5% by weight) and diluted solutions thereof perform well as material 19. Because chlorine bleach is relatively colorless, it is preferred that an artificial coloring of a highly visible hue be added to bleach 19 so that it is readily visible if it and the bleach leak through to the outside of the container.

Disposal device 11 is preferably rather squat. As will be seen, in use device 11 is placed upon a table or other flat surface and the sharp tip of a used medical product is manually forced through the needle-penetrable surface 17. The squat construction of device 11 helps to prevent the device from tipping over during this procedure. For example, the device shown in FIGS. 1 and 2 is generally the same in height as it is in width.

Figure 2:
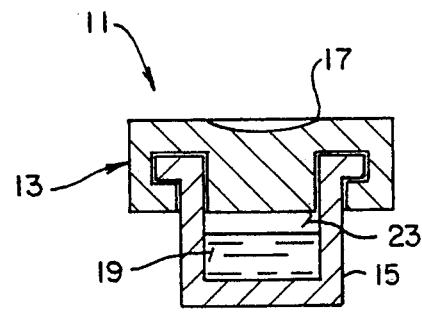
FIG. 2 is a cross-sectional view of the disposal device of FIG. 1.

In FIG. 1, needle-penetrable surface 17 is shown as having a depressed area 21 on the top thereof. This particular depression provides a target for the healthcare professional to use in pushing the tip of the used medical product through the needle-penetrable surface.

Disposal device 11 is designed for single use only, so it is relatively small and contains a relatively small amount of anti-microbic, anti-viral material 19. For example, a width and height of one inch or less is ample for disposal device 11. In fact, a diameter of two centimeters for open-mouthed container 15 and a height of two centimeters or slightly less provides a small, convenient disposal device which contains an adequate amount of anti-microbic, anti-viral material 19.

Six cubic centimeters (cc) of bleach in container 13 provides more than enough extractable or usable material to treat a standard 3 cc syringe/needle combination. In fact a container with a usable or extractable volume of 3 cc, or even 1 cc, of bleach is satisfactory, since it is the tip and bore of the needle which most need to be treated.

It is also preferred that rubber stopper 17 be relatively thick to hold the shaft of the used medical product in place after the tip of the product has been inserted through the stopper into the interior of the container. A thickness of ¼" or so is preferred. The material from which stopper 17 is composed is preferably selected to provide a significant force against axial movement of the shaft of the medical product.

It is also preferred that the various components of disposal device 11 be sterilizable, so that the disposal device may be used in sterile operative fields.

In FIGS. 2, 3, 5, 6, and 7, various mechanical means (overhangs, indentations, and the like) are shown for firmly securing the needle-penetrable surface 17 to open-mouthed container 15. Other means, such as adhesives, could also be used. It is desired that the means of securement provide a water-tight seal between the needle-penetrable surface and the open-mouthed container.

Also shown in these Figs. is an air gap 23 disposed above the anti-microbic, anti-viral material inside the container. This air gap promotes temporary removal, explained below, of a portion of the anti-microbic, anti-viral material 19 from the hollow interior of the container.

Figure 3:
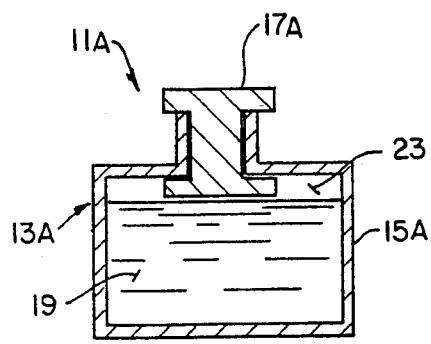
FIG. 3 is a cross-sectional view similar to FIG. 2 of a second embodiment of the disposal device of the present invention.
Figure 4:
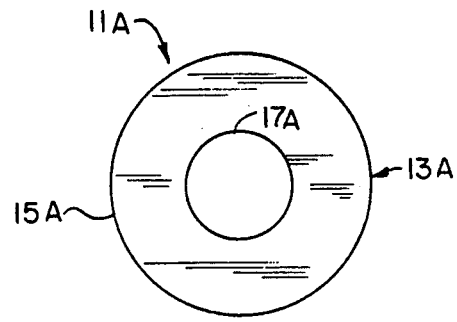
FIG. 4 is a top plan of the disposal device of FIG. 3.

Turning to FIGS. 3 and 4, the container 13A shown in those Figs. has a width or diameter much greater than its height. This particular structure promotes stability of the device during use. Container 13A also has a reduced neck in which is disposed stopper 17A. This structure permits the use of a smaller stopper than that used with the device of FIGS. 1 and 2. Alternatively, it provides a larger quantity of anti-microbic, anti-viral material 19 for use.

Figure 5:
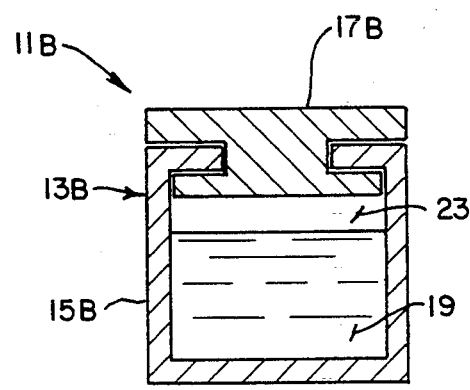
FIG. 5 is a cross-sectional view similar to FIG. 3 of a third embodiment of the disposal device of the present invention.
Figure 6:
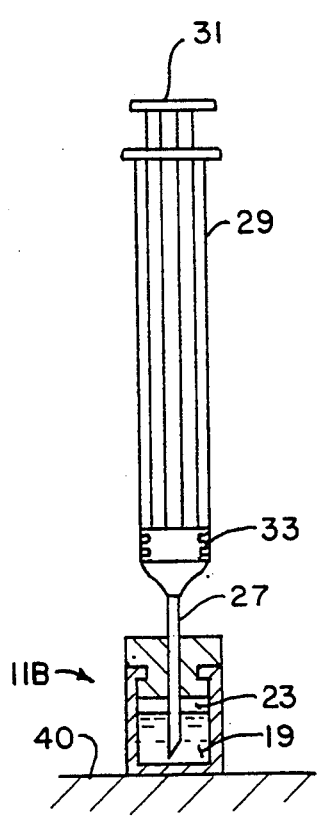
FIG. 6 is an elevation, with parts broken away for clarity, of a disposal product of the present invention.
Figure 7:
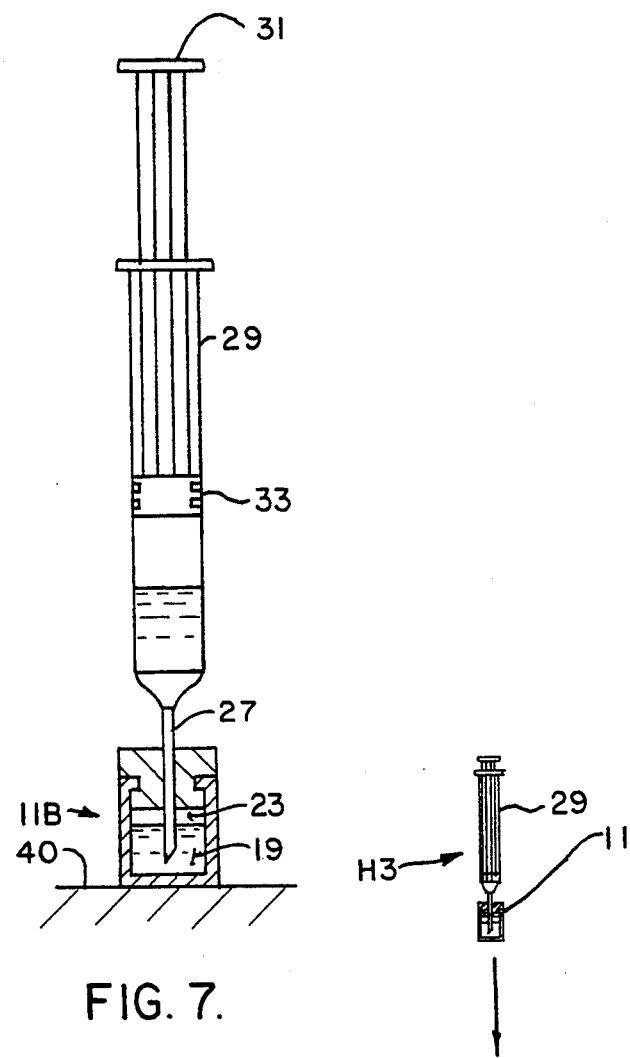
FIG. 7 is an elevation similar to FIG. 7 illustrating the washing or agitating action achievable with the disposal product of the present invention.

Yet a third embodiment of the disposal device of the present invention, this one labelled 11B, is shown in FIGS. 5-7. This device differs from that shown in FIGS. 1 and 2 only in the particular mechanical connection between the open-mouthed container and the plug.

As can be seen from FIGS. 6 and 7, disposal device 11 is especially suited for use with sharp, contaminated medical products, such as a needle 27 shown in those figures. Needle 27 has a sharp tip disposed at the end of a shaft, which shaft defines a hollow bore through the needle. Of course it is also suitable for use with other medical products such as scalpels with have a sharp tip which can penetrate plug 17. Needle 27 is attached in conventional manner to a syringe consisting of a syringe barrel 29 in which is disposed a conventional plunger 31 with a tip 33. Plunger and tip are manually movable from the position shown in FIG. 6 in which the plunger is fully seated in the syringe barrel, to that shown in FIG. 7 in which the plunger is withdrawn somewhat.

In use, the flat base of disposal device 11 is placed on a flat surface such as a table 40 and the tip of the needle or other used medical product is manually forced through plug 17. This is done merely by pushing the syringe downwardly, until the needle tip is well into the anti-microbic, anti-viral liquid. In order to visually confirm this placement, it is desired that the container be transparent, at least in part.

It should be appreciated that when the plunger is moved as illustrated from the position of FIG. 6 to that shown in FIG. 7 and back, anti-microbic, anti-viral liquid 19 is drawn up through the interior bore of needle 27 into syringe barrel 29 and forced back down into the container. It is preferred that approximately 1 cc of bleach 19 be drawn into the syringe barrel. By repeating this reciprocating movement a number of times, e.g., three times, the tip and interior of needle 27 are thoroughly cleaned in the sense that all microbes present therein are killed and viral particles are inactivated by the anti-microbic, anti-viral liquid. In addition, if the anti-microbic, anti-viral material 19 being used has any tendency to separate, this reciprocating and agitating action thoroughly remixes material 19.

In particular, this washing and disinfecting action ensures that the sharp tip of the needle, the most dangerous part, while still sharp, is no longer such a likely source of infection. Even if the disposal device 11 were to come off during subsequent handling, the dangerous tip of the device would no longer be the infectious threat is was before. It should be appreciated that merely disposing the needle tip in disposal device 11 and agitating it (by shaking the syringe/needle combination, for example) provides some of this anti-microbic, anti-viral effect. It is preferred, however, that the anti-microbic, anti-viral liquid actually be drawn up into the syringe barrel to provide maximum protection to the user.

It is intended that at least part of the needle shaft remain outside the disposal device. Device 11 is designed to cover the tip of the needle, not the entire shaft. As a result, it is truly a "one size fits all" device, since the length of the needle being disposed of is irrelevant to proper operation of the device.

Figure 8:
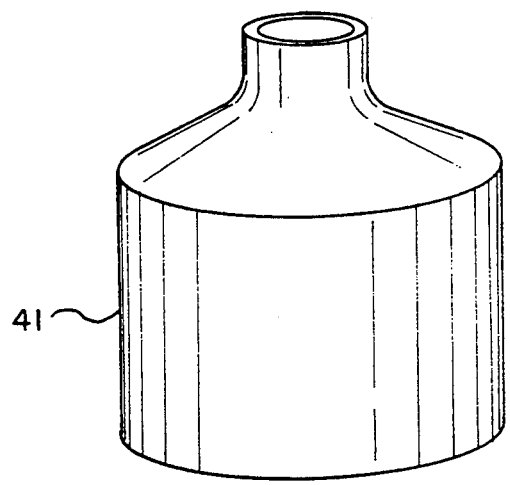
FIG. 8 is a perspective view, on a reduced scale, illustrating proper disposal of the disposal product of FIG. 6.

Once the tip of needle 27 is inserted into disposal device 11 and the desired number of reciprocating movements of the plunger have been accomplished, the needle (with syringe attached) and disposal device as a unit are properly disposed of by placement in a suitable disposal receptacle 41 (FIG. 8). The combination of needle and disposal device is called a disposal product 43. It is intended that the disposal product 43 always be kept intact during disposal to provide maximum protection to those handling potentially infectious wastes. If the parts of the disposal product are separated, however, either accidentally or during subsequent handling of the disposal product, the anti-microbic, anti-viral action described above provides additional protection against infection. This is particularly true since the needle tip and shaft, throughout the length of the interior bore of the needle retain traces of the anti-microbic, anti-viral liquid.

In view of the above, it will be seen that the various objects and features of the invention are achieved and other advantageous results obtained. The examples of the invention given herein are intended to be illustrative only and not to limit the scope of the appended claims.

What is claimed is:

1. A method of disposing of a sharp contaminated medical product having a sharpened tip, such as a needle, comprising:

inserting the sharpened tip of a used medical product such as a needle through a plug into the hollow interior of a container, said hollow interior containing an anti-microbic, anti-viral liquid;

agitating the liquid in the container without manually touching the container to cause at least the tip of the used medical product to come into intimate contact with the anti-microbic, anti-viral liquid; and placing the container and the used medical product as a unit in a disposal receptacle, with the tip of the medical product still disposed in the container.

2. A medical disposal product comprising:

a used medical needle having a sharpened tip at the end of a shaft;

a closed container having a hollow interior, said container having a first surface which is non-coring and readily penetrable by the needle, said container having a second surface opposite the first surface, said second surface being relatively impenetrable by the needle, said container having a total height less than the length of the used medical needle; and an anti-microbic, anti-viral material disposed in the hollow interior of the container;

said tip of the used needle being disposed in the hollow interior of the container and exposed to the anti-microbic, anti-viral material, said needle shaft extending through the first surface of the container and terminating outside the container.

3. The medical disposal product as set forth in claim 2, wherein the first surface is the top of the closed container, the bottom and sides of the closed container being relatively impenetrable by the needle.

4. The medical disposal product as set forth in claim 2, wherein the anti-microbic, anti-viral material is a liquid, further including traces of the anti-microbic, anti-viral liquid throughout the length of the interior bore of the needle.

* * * * *